United States Patent
Marshak

(10) Patent No.: US 9,676,693 B2
(45) Date of Patent: Jun. 13, 2017

(54) BULKY LIGANDS AND METAL COMPOUNDS COMPRISING BULKY LIGANDS

(71) Applicant: Michael Pesek Marshak, Boulder, CO (US)

(72) Inventor: Michael Pesek Marshak, Boulder, CO (US)

( * ) Notice: Subject to any disclaimer, the term of this patent is extended or adjusted under 35 U.S.C. 154(b) by 0 days.

(21) Appl. No.: 14/929,216

(22) Filed: Oct. 30, 2015

(65) Prior Publication Data

US 2017/0121263 A1  May 4, 2017

(51) Int. Cl.
| | |
|---|---|
| *C07C 49/835* | (2006.01) |
| *C07C 49/84* | (2006.01) |
| *C07C 225/20* | (2006.01) |
| *C07C 233/58* | (2006.01) |
| *C07F 7/18* | (2006.01) |
| *C07D 233/58* | (2006.01) |

(52) U.S. Cl.
CPC ............ *C07C 49/835* (2013.01); *C07C 49/84* (2013.01); *C07C 225/20* (2013.01); *C07D 233/58* (2013.01); *C07F 7/1852* (2013.01)

(58) Field of Classification Search
USPC ....................................................... 548/343.5
See application file for complete search history.

(56) References Cited

U.S. PATENT DOCUMENTS 6,706,748 B2 *  3/2004  Kitagawa ............... A01N 43/80
                                                    514/372

* cited by examiner

*Primary Examiner* — Kristin Vajda

(57) ABSTRACT

This disclosure provides, molecular metal catalysts supported by sterically bulky β-diketonate (acac) ligands. Disclosed herein are bulky β-diketonate ligands, methods of making bulky β-diketonate ligands, and methods of making metal catalysts supported by sterically bulky β-diketonate (acac) ligands.

4 Claims, No Drawings

BULKY LIGANDS AND METAL COMPOUNDS COMPRISING BULKY LIGANDS

TECHNICAL FIELD

This disclosure relates to sterically bulky ligands for use in making metal catalysts and metal catalysts including sterically bulky ligands.

BACKGROUND

Reactive molecular metal catalysts are an important class of molecules because they permit chemical transformations not otherwise possible by creating a particular environment around a reactive metal center. This is made possible by using ligands, which provide certain steric and electronic properties at the metal center.

One common technique for creating reactive molecular metal catalysts is to control the steric bulk of the ligand on the metal center. The addition of large functional groups to a ligand can influence reaction rate, coordination number, substrate reactivity, and kinetically stabilize reactive intermediates. Controlling the steric bulk of the ligand has been applied to many different ligand types.

The β-diketonate backbone can be substituted with functional groups in three positions. The most common β-diketone ligand, acetylacetonone, imparts very little steric influence on the resulting metal complex, often forming $M(acac)_3$ or multi-metallic aggregates in solution and solid states.

The acetylacetonate ("acac") ligand is probably the most used β-diketonate. Such acac ligands are among the most pervasive classes of ligands found in inorganic and organometallic chemistry. They have been used and investigated for over a century.

Acetylacetonate ("acac") ligands have been used to coordinate virtually every transition, main group, and f-block element. Metal-acac complexes are commercially available for every transition metal except Tc, W, Re, Os, and Hg and group 13 element (except boron). These complexes commercially available catalysts for polymerization, hydrogenation, oxidation, and condensation reactions, and used as molecular precursors for nanoparticle and thin film materials.

Although this ligand class has been explored for over a century, the community has never developed an effective way of introducing large steric bulk onto β-diketonate (acac) ligands. Accordingly, the molecular metal catalyst community has not benefited from molecular metal catalysts supported by sterically bulky β-diketonate (acac) ligands.

DETAILED DESCRIPTION

This disclosure provides, molecular metal catalysts supported by sterically bulky β-diketonate (acac) ligands.

Disclosed herein are bulky β-diketonate ligands, methods of making bulky β-diketonate ligands, and methods of making metal catalysts supported by sterically bulky β-diketonate (acac) ligands.

Also disclosed herein is the use of large alkyl (e.g., tertiary butyl) or aryl groups larger than mesityl, such as the 2,6-diphenylphenyl (m-terphenyl) group in the 1, 2, and/or 3 positions of the traditional acac scaffold. Such bulky ligands are useful for preventing aggregation of the molecular metal catalysts and enable isolation of monomeric bis-acac main group and transition metals. As shown in the figure below, the bis-acac metal complexes can adopt a cis or trans coordination with respect to each other.

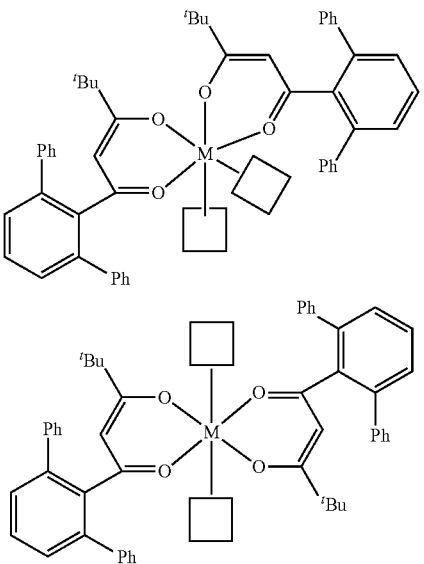

In the figure above, the square/box bonded to the metal ("M") designates a free coordination site.

These new bulky ligands are useful for making metal catalysts for olefin polymerization, hydroformylation, and oxidation.

Additionally, metal complexes of bulky aryl-substituted acac are useful for performing catalysis in olefin polymerization, oligomerization, hydroformylation, hydroarylation, hydrogenation, and oxidation.

Furthermore, this disclosure provides binaphthyl-substituted acac and methods of using the same to perform enantioselective catalysis.

As shown in the two examples (A and B) below, Terphenyl-substituted acac ligands can be synthesized by treatment of m-dichlorobenzene with aryl-Grignard, then subsequent condensation to afford the β-diketone.

Example A

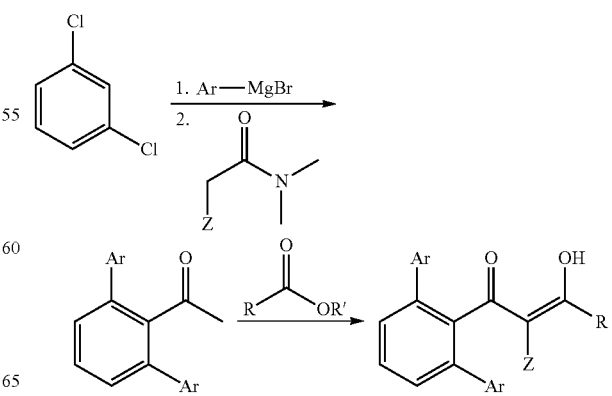

Example B

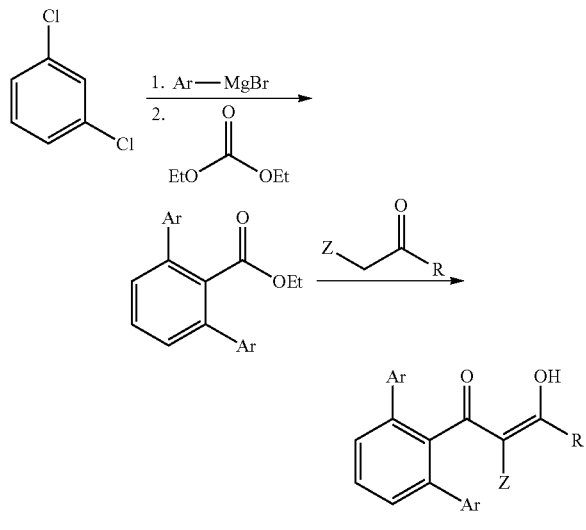

The disclosed bulky acac molecules can be used to make metal complexes via a salt metathesis of the alkali-metal acac ligand with corresponding metal halides in a 2:1 ratio. This salt metathesis reaction provides a series of first-row transition metal complexes: $(L_1)_2TiCl_2$, $(L_1)_2VCl_2$, $(L_1)_2CrCl(THF)$, $(L_1)_2Mn(THF)_2$, $(L_1)_2Fe(THF)_2$, $(L_1)_2Co(THF)$, $(L_1)_2Ni$, $(L_1)_2Cu$, and $(L_1)_2Zn$; wherein $L_1$ is a bulky ligand as disclosed herein.

Disclosed herein are methods of synthesizing terphenyl-substituted β-dithionate, β-diketiminate, and pyrazolyl ligand derivatives having the following structural formulae:

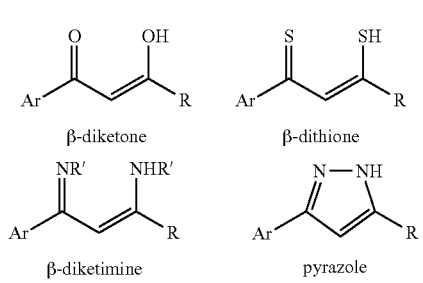

β-diketonates are precursors to a number of other ligand derivatives including β-dithionates, β-diketiminates, and pyrazoles. The β-dithionates are synthesized by treatment with $H_2S$, and provide a softer ligand environment for late transition metals and main group elements. See, e.g., Cox, M.; Darken, J. Coord. Chem. Rev. 1971, 7, 29-58. Although β-diketiminates have been investigated with terphenyl groups ligated to the nitrogen atoms, placement of terphenyl on the carbon backbone should permit the use of smaller alkyl groups on the nitrogen atoms, which would provide a more electron-rich ligand field to the corresponding metal atom.

In the figures above, the double bonding character of the ligand backbone can be structurally depicted in a variety of ways.

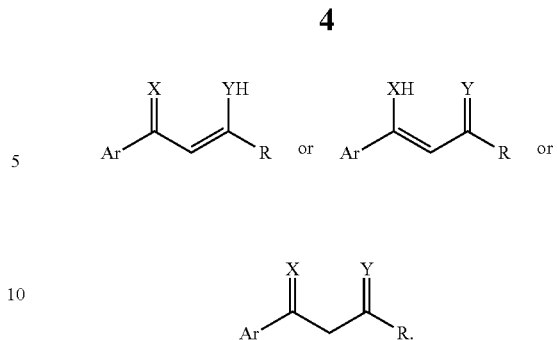

For the structures and formula disclosed and claimed herein, the structural formulas are drawn without specifically pointing out the double bond character in the backbone. It should be understood that the structural figures used herein include double bond character in the ligand (e.g., ac-ac) backbone. For example:

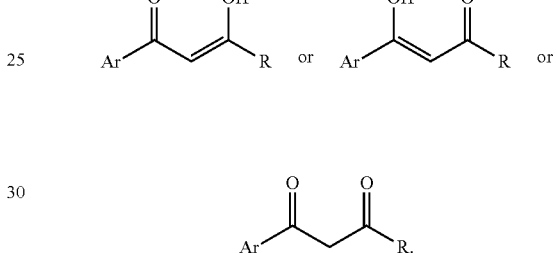

Also disclosed herein are pyrazole complexes, which can be synthesized by reaction of the β-diketone with hydrazine.

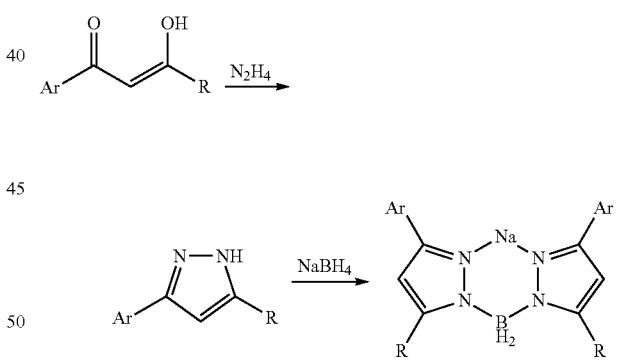

Ligands such as bispyrazolyl borate and bispyrazolyl methane ligands will be generated from the bulky pyrazoles using procedures reported in the literature. See, e.g., Trofimenko, S. Scorpionates: The Coordination Chemistry of Polypyrazolylborate Ligands; Imperial College Press, 1999.

The compounds disclosed herein can be verified by characterization tools commonly used in the art, including NMR, IR, UV/VIS, and single crystal X-ray crystallography. Structural characterization can be used to show the exact coordination environment, including whether ligands (L) are in a cis or trans coordination arrangement on the metal center.

Disclosed herein is a compound having the following structural formula (I):

I

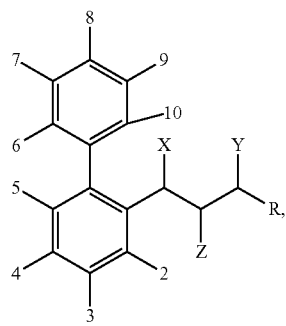

wherein X is chosen from O, S, or N;

Y is chosen from O, S, or N;

Z is H, or a substituted or unsubstituted alkyl group;

R is chosen from a substituted or unsubstituted C1-C24 alkyl, a substituted or unsubstituted aryl group;

each of the positions 2, 3, 4, 5, 6, 7, 8, 9, and 10 is chosen from a substituted or unsubstituted alkyl group, a substituted or unsubstituted aryl group, or $OSiQ_3$;

wherein none of the groups X, Y, Z, or R is connected to another group Z or R by a covalent bond;

wherein Q is chosen from a substituted or unsubstituted alkyl group or a substituted or unsubstituted aryl group;

provided that R does not include a non-aromatic olefin;

provided that neither position R nor position 10 includes a carbonyl; and provided that, when R is phenyl, then position 4 is neither aryl nor substituted aryl.

As used herein, the term "non-aromatic olefin" means an unsaturated hydrocarbon not part of an aromatic ring, for example a straight chain alkene.

Within this application, where Y is chosen to by "N," it should be understood that "N" would also include an —NR group or an —NH group, provided that the position designated by the group "Y" includes a nitrogen atom (N) at that position. For example, selecting "N" for Y would include any of the following three examples:

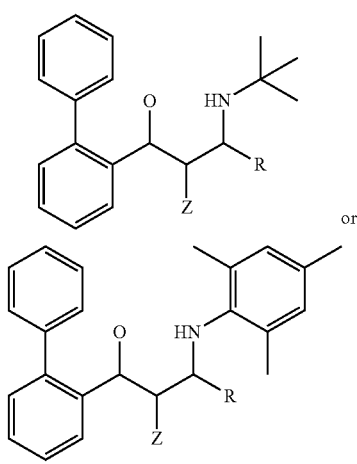

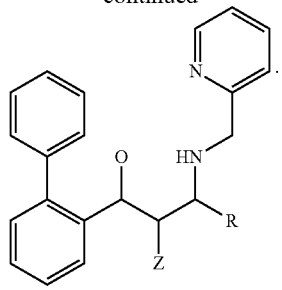

Within this application, where X is chosen to by "N," it should be understood that "N" would also include an —NR group or an —NH group, provided that the position designated by the group "X" includes a nitrogen atom (N) at that position. For example, selecting "N" for X would include any of the following three examples:

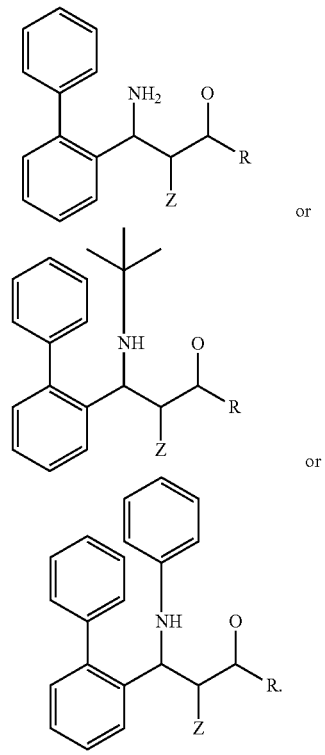

As used herein, the term "substituted alkyl group" means a linear or branched hydrocarbon containing between 1 and 24 carbon atoms, and at least one non-carbon, non-hydrogen atom.

As used herein, the term "unsubstituted alkyl group" means a linear or branched hydrocarbon containing between 1 and 24 carbon atoms.

As used herein, the term "substituted C1-C24 alkyl" means a linear or branched hydrocarbon containing between 1 and 24 carbon atoms and at least one non-carbon, non-hydrogen atom.

As used herein, the term "unsubstituted C1-C24 alkyl" means a linear or branched hydrocarbon containing between 1 and 24 carbon atoms.

As used herein, the term "substituted aryl group" means an aromatic ring containing an additional alkyl, substituted alkyl, aryl, or substituted aryl group or at least one non-carbon, non-hydrogen atom.

As used herein, the term "unsubstituted aryl group" means an aromatic ring. In the above disclosed compounds of formula I, none of the groups X, Y, Z, or R is connected to another group Z, or R by a covalent bond. The phrase "none of the groups X, Y, Z, or R is connected to another group Z, or R by a covalent bond" is used to distinguish the compounds of formula I from compounds such as

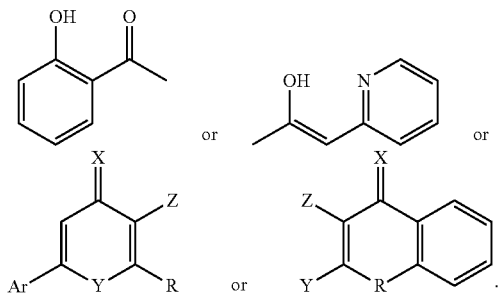

In one embodiment of the disclosure, the compound of formula I, has each of the groups X and Y bonded to a single metal atom. As used herein the phrase "each of the groups X and Y bonded to a single metal atom" means that each of the groups X and Y in the compound is chemically connected to the same "single" metal center as illustrated in the following exemplary chemical structures:

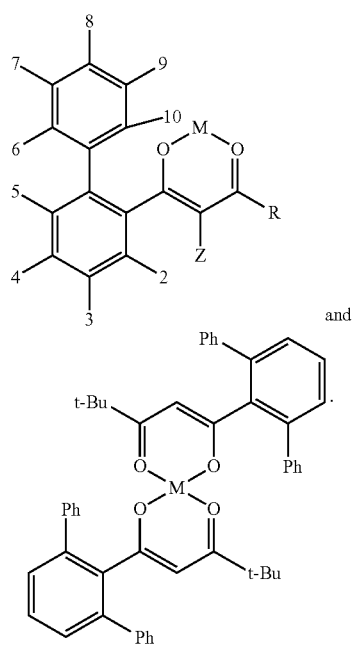

In one embodiment, the said single metal atom is chosen from Li, Na, K, Rb, Cs, Be, Mg, Ca, Sr, Ba, Sc, Y, La, Ti, V, Cr, Mn, Fe, Co, Ni, Cu, Zn, Zr, Nb, Mo, Ru, Rh, Pd, Ag, Cd, Hf, Ta, W, Re, Os, Ir, Pt, Au, Al, Ga, In, Tl, Ge, Sn, Pb, P, As, Sb, or Bi.

Disclosed herein is a compound of the following formula (II):

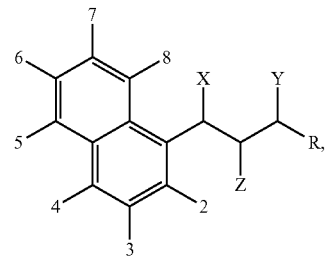

wherein X is chosen from O, S, or N;
Y is chosen from O, S, or N;
Z is a substituted or unsubstituted alkyl group or a substituted or unsubstituted aryl group;
R is chosen from a substituted or unsubstituted C1-C24 alkyl, a substituted or unsubstituted aryl group;
wherein none of the groups X, Y, Z, or R is connected to another group Z or R by a covalent bond;
wherein the position 2 is chosen from substituted or unsubstituted C2-C24 alkyl, OSiQ$_3$, and substituted or unsubstituted aryl;
wherein the position 3 is chosen from substituted or unsubstituted C2-C24 alkyl, OSiQ$_3$, and substituted or unsubstituted aryl;
wherein the position 4 is chosen from substituted or unsubstituted C2-C24 alkyl, OSiQ$_3$, and substituted or unsubstituted aryl;
wherein the position 5 is chosen from substituted or unsubstituted C1-C24 alkyl, OSiQ$_3$, and substituted or unsubstituted aryl;
wherein the position 6 is chosen from substituted or unsubstituted C1-C24 alkyl, OSiQ$_3$, and substituted or unsubstituted aryl;
wherein the position 7 is chosen from substituted or unsubstituted C2 or C4-C24 alkyl, OSiQ$_3$, and substituted or unsubstituted aryl; and
wherein the position 8 is chosen from substituted or unsubstituted C1-C24 alkyl, OSiQ$_3$, and substituted or unsubstituted aryl.

In one embodiment of the disclosure, the compound of formula II, has each of the groups X and Y bonded to a single metal atom. In one embodiment, the said single metal atom is chosen from Li, Na, K, Rb, Cs, Be, Mg, Ca, Sr, Ba, Sc, Y, La, Ti, V, Cr, Mn, Fe, Co, Ni, Cu, Zn, Zr, Nb, Mo, Ru, Rh, Pd, Ag, Cd, Hf, Ta, W, Re, Os, Ir, Pt, Au, Al, Ga, In, Tl, Ge, Sn, Pb, P, As, Sb, or Bi.

Disclosed herein is a compound of the following formula III:

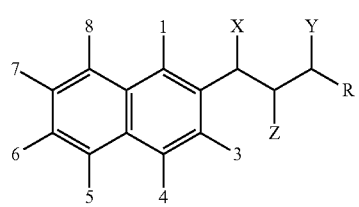

wherein X is chosen from O, S, or N;
Y is chosen from O, S, or N;
Z is a substituted or unsubstituted alkyl group;
R is chosen from a substituted or unsubstituted C1-C24 alkyl, a substituted or unsubstituted aryl group;

wherein none of the groups X, Y, Z, or R is connected to another group Z or R by a covalent bond;

wherein position 1 is chosen from substituted or unsubstituted C2-C24 alkyl, OSiQ$_3$, and substituted or unsubstituted aryl;

wherein position 3 is chosen from substituted or unsubstituted C2-C24 alkyl, OSiQ$_3$, and substituted or unsubstituted aryl;

wherein position 4 is chosen from substituted or unsubstituted C2-C24 alkyl, OSiQ$_3$, and substituted or unsubstituted aryl;

wherein position 5 is chosen from substituted or unsubstituted C1-C24 alkyl, OSiQ$_3$, and substituted or unsubstituted aryl;

wherein position 6 is chosen from substituted or unsubstituted C2-C24 alkyl, OSiQ$_3$, and substituted or unsubstituted aryl;

wherein position 7 is chosen from substituted or unsubstituted C2-C24 alkyl, OSiQ$_3$, and substituted or unsubstituted aryl; and wherein position 8 is chosen from substituted or unsubstituted C2-C24 alkyl, OSiQ$_3$, and substituted or unsubstituted aryl.

In one embodiment of the disclosure, the compound of formula III, has each of the groups X and Y bonded to a single metal atom. In one embodiment, the said single metal atom is chosen from Li, Na, K, Rb, Cs, Be, Mg, Ca, Sr, Ba, Sc, Y, La, Ti, V, Cr, Mn, Fe, Co, Ni, Cu, Zn, Zr, Nb, Mo, Ru, Rh, Pd, Ag, Cd, Hf, Ta, W, Re, Os, Ir, Pt, Au, Al, Ga, In, Tl, Ge, Sn, Pb, P, As, Sb, or Bi.

Disclosed herein is a compound of the following formula IV:

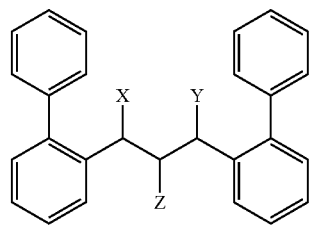

IV wherein X is chosen from O, S, or N;
Y is chosen from O, S, or N;
Z is a substituted or unsubstituted alkyl group;
wherein none of the groups X, Y, or Z is connected to another group X, Y, or Z by a covalent bond;
each position on the biphenyl rings depicted in formula IV is chosen from H or a biphenyl substituent; and
and wherein "biphenyl substituent" is chosen from a substituted or unsubstituted C1-C24 alkyl, a substituted or unsubstituted aryl group, or OSiQ$_3$.

In one embodiment of the disclosure, the compound of formula IV, has each of the groups X and Y bonded to a single metal atom. In one embodiment, the said single metal atom is chosen from Li, Na, K, Rb, Cs, Be, Mg, Ca, Sr, Ba, Sc, Y, La, Ti, V, Cr, Mn, Fe, Co, Ni, Cu, Zn, Zr, Nb, Mo, Ru, Rh, Pd, Ag, Cd, Hf, Ta, W, Re, Os, Ir, Pt, Au, Al, Ga, In, Tl, Ge, Sn, Pb, P, As, Sb, or Bi.

Disclosed herein is a compound of the following structural formula V:

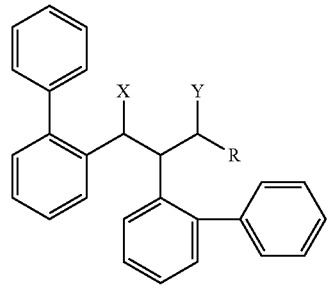

V wherein X is chosen from O, S, or N;
Y is chosen from O, S, or N;
R is chosen from a substituted or unsubstituted C1-C24 alkyl, a substituted or unsubstituted aryl group, or OSiQ$_3$;
wherein none of the groups X, Y, or R is connected to another group X, Y, R or a biphenyl group for formula V by a covalent bond;
wherein each position on the biphenyl rings depicted in formula IV is chosen from H or a biphenyl substituent; and and wherein "biphenyl substituent" is chosen from a substituted or unsubstituted C1-C24 alkyl, a substituted or unsubstituted aryl group, or OSiQ$_3$.

In one embodiment of the disclosure, the compound of formula V, has each of the groups X and Y bonded to a single metal atom. In one embodiment, the said single metal atom is chosen from Li, Na, K, Rb, Cs, Be, Mg, Ca, Sr, Ba, Sc, Y, La, Ti, V, Cr, Mn, Fe, Co, Ni, Cu, Zn, Zr, Nb, Mo, Ru, Rh, Pd, Ag, Cd, Hf, Ta, W, Re, Os, Ir, Pt, Au, Al, Ga, In, Tl, Ge, Sn, Pb, P, As, Sb, or Bi.

Disclosed herein is a compound of the following formula VI:

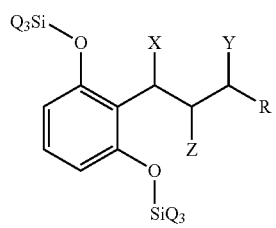

VI wherein X is chosen from O, S, or N;
Y is chosen from O, S, or N;
Z is a substituted or unsubstituted alkyl or aryl group;
R is chosen from a substituted or unsubstituted C1-C24 alkyl, a substituted or unsubstituted aryl group;
wherein none of the groups X, Y, Z, or R is connected to another group Z or R by a covalent bond;
Q is chosen from a substituted or unsubstituted alkyl or aryl group; each position on the phenyl ring depicted in formula VI is chosen from H or a phenyl substituent; and
wherein "phenyl substituent" is chosen from a substituted or unsubstituted alkyl, aryl group, or OSiQ$_3$.

In one embodiment of the disclosure, the compound of formula VI, has each of the groups X and Y bonded to a single metal atom. In one embodiment, the said single metal atom is chosen from Li, Na, K, Rb, Cs, Be, Mg, Ca, Sr, Ba, Sc, Y, La, Ti, V, Cr, Mn, Fe, Co, Ni, Cu, Zn, Zr, Nb, Mo, Ru, Rh, Pd, Ag, Cd, Hf, Ta, W, Re, Os, Ir, Pt, Au, Al, Ga, In, Tl, Ge, Sn, Pb, P, As, Sb, or Bi.

Disclosed herein is a compound of the following structural formula:

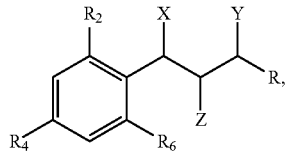

wherein X is chosen from O, S, or N;
Y is chosen from O, S, or N;
Z is a substituted or unsubstituted alkyl group;
R is independently chosen from a substituted or unsubstituted C1-C24 alkyl, a substituted or unsubstituted aryl group
none of the groups X, Y, Z, or R is connected to another group Z or R by a covalent bond;
each of R2, R4, and R6 is independently chosen from H, substituted phenyl, unsubstituted phenyl or C1-C24 alkyl;
Q is chosen from a substituted or unsubstituted alkyl or aryl group; provided that where R is phenyl, R4 is not methyl or phenyl.

In one embodiment of the above described compound has each of the groups X and Y bonded to a single metal atom. In one embodiment, the said single metal atom is chosen from Li, Na, K, Rb, Cs, Be, Mg, Ca, Sr, Ba, Sc, Y, La, Ti, V, Cr, Mn, Fe, Co, Ni, Cu, Zn, Zr, Nb, Mo, Ru, Rh, Pd, Ag, Cd, Hf, Ta, W, Re, Os, Ir, Pt, Au, Al, Ga, In, Tl, Ge, Sn, Pb, P, As, Sb, or Bi.

Disclosed herein is a compound of the following structural formula,

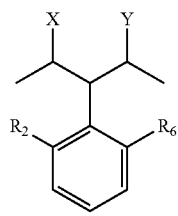

wherein each of R2 and R6 is a group of the formula OSiQ$_3$
wherein X is chosen from O, S, or N;
Y is chosen from O, S, or N; and
Q is chosen from a substituted or unsubstituted alkyl or aryl group.

In one embodiment of the above described compound has each of the groups X and Y bonded to a single metal atom. In one embodiment, the said single metal atom is chosen from Li, Na, K, Rb, Cs, Be, Mg, Ca, Sr, Ba, Sc, Y, La, Ti, V, Cr, Mn, Fe, Co, Ni, Cu, Zn, Zr, Nb, Mo, Ru, Rh, Pd, Ag, Cd, Hf, Ta, W, Re, Os, Ir, Pt, Au, Al, Ga, In, Tl, Ge, Sn, Pb, P, As, Sb, or Bi.

Disclosed herein is a compound of the following structural formula XI:

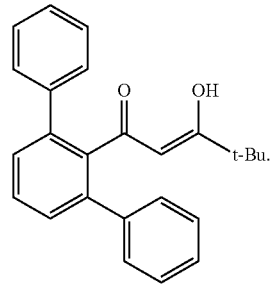 [SMILES: CC(C)(C)/C(O)=C/C(=O)c1c(-c2ccccc2)cccc1-c1ccccc1]

Disclosed herein is a compound of the following structural formula XII:

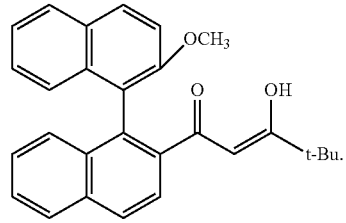 [SMILES: COc1ccc2ccccc2c1-c1c(C(=O)/C=C(\O)C(C)(C)C)ccc2ccccc12]

Disclosed herein is a compound of the following structural formula XIII:

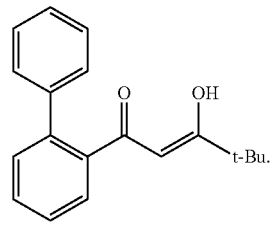 [SMILES: CC(C)(C)/C(O)=C/C(=O)c1ccccc1-c1ccccc1]

Disclosed herein is a compound of the following structural formula XIV:

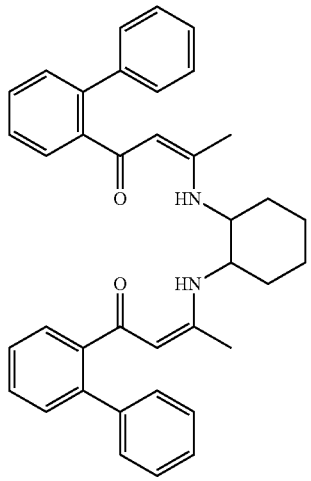

Disclosed herein is a compound of the following structural formula XV:

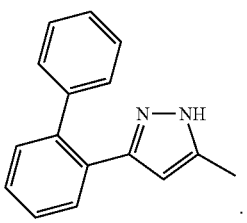 [SMILES: Cc1cc(-c2ccccc2-c2ccccc2)n[nH]1]

Disclosed herein is a compound of the following structural formula XVI:

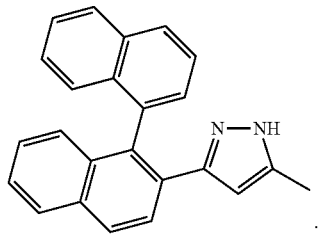 [SMILES: Cc1cc(-c2ccc3ccccc3c2-c2cccc3ccccc23)n[nH]1]

Disclosed herein is a neutral or charged compound of the following structural formula:

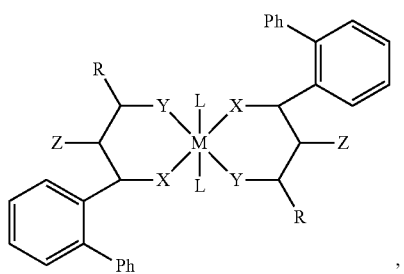

wherein each X is independently chosen from O, S, or N;

each Y is chosen from O, S, or N;

each Z is independently chosen from a substituted or unsubstituted alkyl group;

each R is independently chosen from a substituted or unsubstituted C1-C24 alkyl, a substituted or unsubstituted aryl group;

none of the groups X, Y, Z, or R is connected to another group Z or R by a covalent bond;

M is chosen from Li, Na, K, Rb, Cs, Be, Mg, Ca, Sr, Ba, Sc, Y, La, Ti, V, Cr, Mn, Fe, Co, Ni, Cu, Zn, Zr, Nb, Mo, Ru, Rh, Pd, Ag, Cd, Hf, Ta, W, Re, Os, Ir, Pt, Au, Al, Ga, In, Tl, Ge, Sn, Pb, P, As, Sb, or Bi; and each L is independently chosen from a common neutral or charged ligand.

In one embodiment, the phrase "each L is independently chosen from a common neutral or charged ligand" should also be understood to include circumstances where L is nothing, i.e., wherein the compound defined does not include any ligand at that position.

Disclosed herein is a neutral or charged compound of the following structural formula:

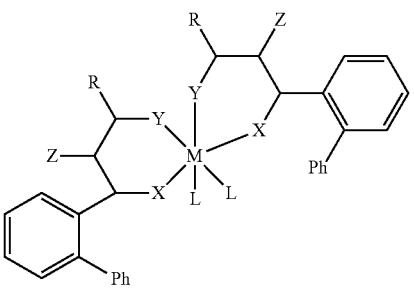

wherein each X is independently chosen from O, S, or N;

each Y is chosen from O, S, or N;

each Z is independently chosen from a substituted or unsubstituted alkyl group;

each R is independently chosen from a substituted or unsubstituted C1-C24 alkyl, a substituted or unsubstituted aryl group;

none of the groups Z or R is connected to another group X, Z or R by a covalent bond;

M is chosen from Li, Na, K, Rb, Cs, Be, Mg, Ca, Sr, Ba, Sc, Y, La, Ti, V, Cr, Mn, Fe, Co, Ni, Cu, Zn, Zr, Nb, Mo, Ru, Rh, Pd, Ag, Cd, Hf, Ta, W, Re, Os, Ir, Pt, Au, Al, Ga, In, Tl, Ge, Sn, Pb, P, As, Sb, or Bi; and each L is independently chosen from a common neutral or charged ligand.

Disclosed herein is a neutral or charged compound of the following structural formula:

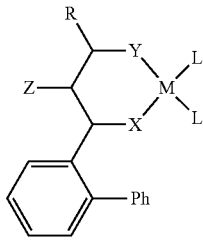

wherein each X is independently chosen from O, S, or N;

each Y is chosen from O, S, or N;

each Z is independently chosen from a substituted or unsubstituted alkyl group;

each R is independently chosen from a substituted or unsubstituted C1-C24 alkyl, a substituted or unsubstituted aryl group;

none of the groups Z or R is connected to another group X, Z or R by a covalent bond;

M is chosen from Li, Na, K, Rb, Cs, Be, Mg, Ca, Sr, Ba, Sc, Y, La, Ti, V, Cr, Mn, Fe, Co, Ni, Cu, Zn, Zr, Nb, Mo, Ru, Rh, Pd, Ag, Cd, Hf, Ta, W, Re, Os, Ir, Pt, Au, Al, Ga, In, Tl, Ge, Sn, Pb, P, As, Sb, or Bi; and each L is independently chosen from a common neutral or charged ligand.

Disclosed herein is a method of making bulky ligands, comprising treating a meta-dihalophenyl compound with an aryl Grignard reagent; quenching the resulting terphenyl Grignard with dimethylacetamide or other Z-substituted derivative; and condensing the resulting aryl ketone with an ester. Within the context of this disclosure, anhydrides, e.g., acetic anhydride may be used to quench Grignard reagents to create compounds useful for making ligands described herein.

Disclosed herein is a method of making bulky ligands, comprising treating a meta-dihalophenyl compound with an aryl Grignard reagent; quenching the resulting meta-terphenyl Grignard with diethylcarbonate (or similar); and condensing the resulting ethyl aryloate with a Z and/or R-substituted methyl ketone.

As used herein, the term "quenching the resulting meta-terphenyl Grignard with diethylcarbonate" means addition of a solution of diethylcarbonate to a solution of meta-terphenyl Grignard to generate ethyl aryloate. It should be understood that compounds similar to diethylcarbonate may be used instead of diethylcarbonate. For example, dimethylcarbonate, diphenylcarbonate, or $CO_2$.

As used herein, the term "condensing the resulting ethyl aryloate with a Z and/or R-substituted methyl ketone" means performing a Claisen condensation reaction by treating an ester with a ketone to produce a β-diketone (acac).

EXAMPLES

The specific examples provided below are included to illustrate certain embodiments of this disclosure. These specific examples should not be read a limiting because a person of ordinary skill in the art would appreciate that alkyl or aryl substituents could be included by substituting a C—H bond for an alkyl or aryl group and following the general synthetic guidance provided by this disclosure. Likewise, the solvents, temperatures, times, and reactions conditions should serve only to illustrate specific examples of how to make and use the compounds of this disclosure. They could be varied as commonly understood in the art.

Example 1

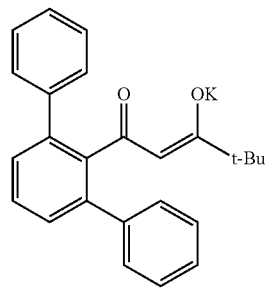

A THF solution of m-terphenyl Grignard, is prepared according to the literature procedure by addition of a solution of butyllithium (1 molar equivalent) to a THF solution of 1,3-dichlorobenzene at −70° C., followed by addition of a solution of phenyl magnesium bromide (2 molar equivalents) at −84° C. and warming to reflux (Saednya and Hart, *Synthesis,* 1996, 1455-1458.), and added to 1.2 equivalents of diethyl carbonate in THF. The solvent is removed under vacuum, and the solid is extracted with toluene, filtered, and concentrated. The aryl ester product is then purified by commonly used purification techniques. For example, the product may be precipitated upon addition of hexane. Alternatively it may be purified via chromatography.

THF solution of pinacolone is added dropwise to a suspension of potassium hydride in THF at 0° C. The effervescent solution releases hydrogen. To this solution is added the above m-terphenyl ethyl ester. The solution is stirred at room temperature for 1 hour and then refluxed for 24 hours. The solvent is then removed under vacuum to give the potassium acac salt, which can be recrystallized from THF/hexane.

Example 2

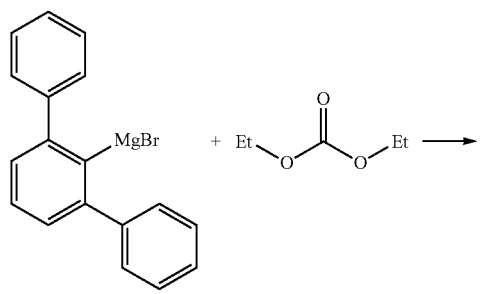

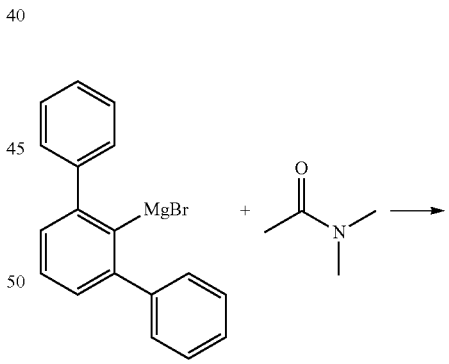

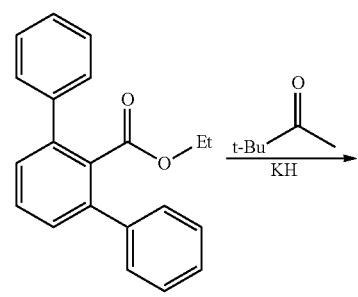

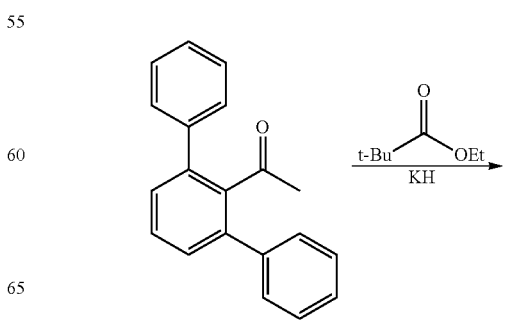

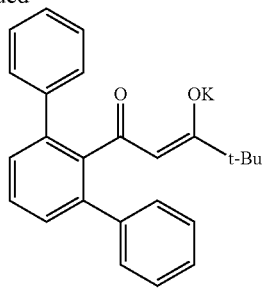

A THF solution of m-terphenyl Grignard, is prepared according to the literature procedure by addition of a solution of butyllithium (1 molar equivalent) to a THF solution of 1,3-dichlorobenzene at −70° C., followed by addition of a solution of phenyl magnesium bromide (2 molar equivalents) at −84° C. and warming to reflux (Saednya and Hart, *Synthesis*, 1996, 1455-1458.), and added to an excess of dimethylacetamide in THF. The solvent is removed under vacuum, and the solid is extracted with toluene, filtered, and concentrated. The aryl ketone product is precipitated upon addition of hexane.

A THF solution of the aryl ketone is added dropwise to a suspension of potassium hydride in THF at 0° C. The effervescent solution releases hydrogen. To this solution is added ethyl pivalate. The solution is stirred at room temperature for 1 hour and then refluxed for 24 hours. The solvent is then removed under vacuum to give the potassium acac salt, which can be recrystallized from THF/hexane.

Example 3

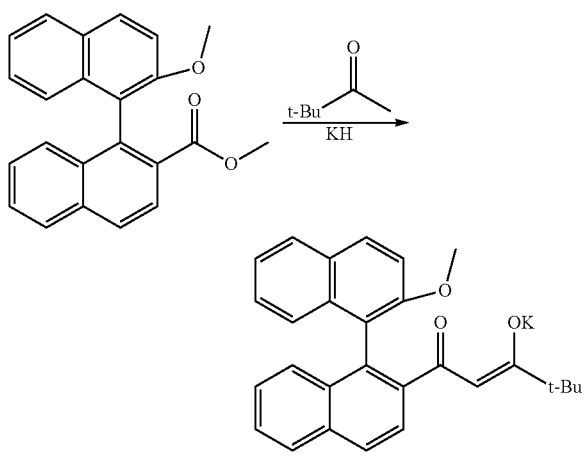

A THF solution of pinacolone is added dropwise to a suspension of potassium hydride in THF at 0° C. The effervescent solution releases hydrogen. To this solution is added the above binaphthyl ethyl ester, prepared according to the literature procedure from the reaction of methyl 1-methoxy-2-naphthoate with (2-methoxynaphthalen-1-yl) magnesium bromide (Hattori et al. Bull. Chem. Soc. Japan 1993, 66, 613-622.). The solution is stirred at room temperature for 1 hour and then refluxed for 24 hours. The solvent is then removed under vacuum to give the potassium acac salt, which can be recrystallized from THF/hexane.

Example 4

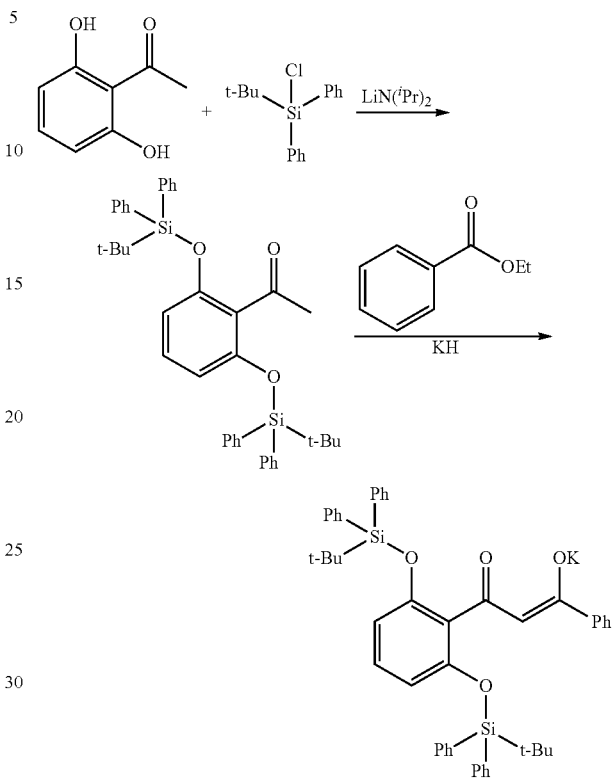

A THF solution of 2,6-dihydroxy-acetonphone was treated with tert-butyl-diphenylsilyl chloride and Lithium diisopropyl amide to generate 2,6-bis(tert-butyldiphenylsiloxy)acetophenone, in an analogous procedure to Ref (Morton, J. G. M. et al. *Tetrahedron Letters*, 2009, 50, 1684-1686.). The 2,6-bis(tert-butyldiphenylsiloxy)acetophenone was treated with potassium hydride in THF at 0° C. The effervescent solution releases hydrogen. To this solution was added ethyl benzoate. The solution is stirred at room temperature for 1 hour and then refluxed for 24 hours. The solvent is then removed under vacuum to give the potassium acac salt, which can be recrystallized from THF/hexane.

Example 5

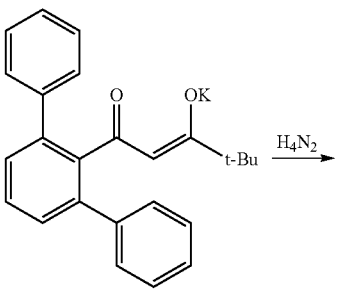

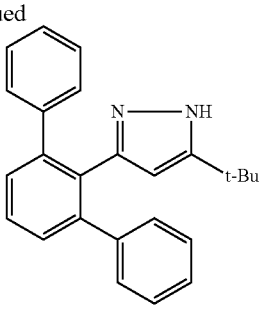

The acac molecule from the above example 1 was dissolved in methanol and hydrazine hydrate was added dropwise. The corresponding pyrazole species precipitated from solution.

Example 6

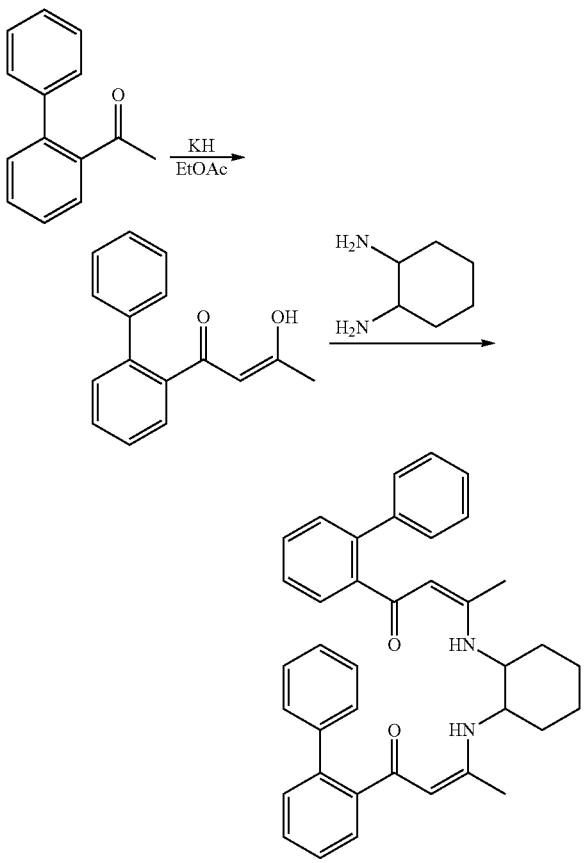

A THF solution of 2-Acetylbiphenyl is added dropwise to a suspension of potassium hydride in THF at 0° C. The effervescent solution releases hydrogen. To this solution is added ethyl acetate, and the reaction is warmed to room temperature. Dilute hydrochloric acid is added to precipitate 1-(1-1'-biphenyl)-1,3-butane-dioneate.

1-(1-1'-biphenyl)-1,3-butane-dione is dissolved in benzene and refluxed in a Dean-Stark apparatus with 0.5 equivalents of racemic 1,2-cyclohexanediamine. Upon removal of the solvent, the ligand shown above is isolated.

The following selection of references would provide a skilled artisan with the adequate background information necessary for implementing the synthetic methods disclosed herein:

(1) Vigato, P. A.; Peruzzo, V.; Tamburini, S. *Coord. Chem. Rev.* 2009, 253, 1099-1201.
(2) Cotton, F. A.; Elder, R. C. *Inorg. Chem.* 1965, 4, 1145-1151.
(3) Cotton, F. A.; Wise, J. J. *Inorg. Chem.* 1966, 5, 1200-1207.
(4) Cui Zhang; Peiju Yang; Yue Yang; Xiaojuan Huang; Xiao-Juan Yang; Biao Wu *Synth. Commun.* 2008, 38, 2349-2356.
(5) Cox, M.; Darken, J. *Coord. Chem. Rev.* 1971, 7, 29-58.
(6) Trofimenko, S. *Scorpionates: The Coordination Chemistry of Polypyrazolylborate Ligands*; Imperial College Press, 1999.
(7) Saednya, A.; Hart, H. *Synthesis* 1996, 1996, 1455-1458.
(8) Power, P. P. *J. Organomet. Chem.* 2004, 689, 3904-3919.
(9) Glidewell, C.; Turner, G. M.; Ferguson, G. *Acta Crystallogr. C* 1996, 52, 11-14.
(10) Ferguson, G.; Glidewell, C. *Acta Crystallogr. C* 2001, 57, 264-265.
(11) Shmulinson, M.; Galan-Fereres, M.; Lisovskii, A.; Nelkenbaum, E.; Semiat, R.; Eisen, M. S. *Organometallics* 2000, 19, 1208-1210.
(12) Gornshtein, F.; Kapon, M.; Botoshansky, M.; Eisen, M. S. *Organometallics* 2007, 26, 497-507.
(13) Maurya, M. R. *Coord. Chem. Rev.* 2003, 237, 163-181.
(14) Hedegaard, E. D.; Schau-Magnussen, M.; Bendix, J. *Inorg. Chem. Commun.* 2011, 14, 719-721.
(15) McGarrigle, E. M.; Gilheany, D. G. *Chem Rev* 2005, 105, 1563-1602.
(16) Fürstner, A.; Leitner, A. *Angew. Chem. Int. Ed.* 2002, 41, 609-612.
(17) Moreau, B.; Wu, J. Y.; Ritter, T. *Org. Lett.* 2009, 11, 337-339.
(18) Debuigne, A.; Poli, R.; Jerome, C.; Jerome, R.; Detrembleur, C. *Prog. Polym. Sci.* 2009, 34, 211-239.

The above listed 18 references are hereby incorporated by reference in their entirety.

I claim:
1. A compound having the following structural formula (I):

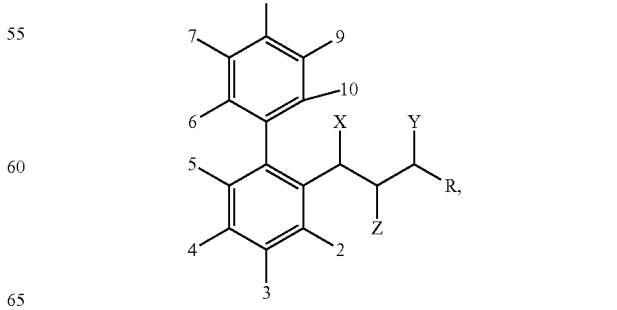

wherein X is chosen from O, S, or N;

Y is chosen from O, S, or N;

Z is H, or a substituted or unsubstituted alkyl group;

R is chosen from a substituted or unsubstituted C1-C24 alkyl, a substituted or unsubstituted aryl group;

each of the positions 2, 3, 4, 5, 6, 7, 8, 9, and 10 is chosen from hydrogen, a substituted or unsubstituted alkyl group, a substituted or unsubstituted aryl group, or $OSiQ_3$;

wherein none of the groups X, Y, Z, or R is connected to another group Z, or R by a covalent bond;

wherein Q is chosen from a substituted or unsubstituted alkyl group or a substituted or unsubstituted aryl group;

provided that R does not include a non-aromatic olefin;

provided that neither position R nor position 10 includes a carbonyl;

provided that, when R is phenyl, then position 4 is neither aryl nor substituted aryl;

provided that R is not

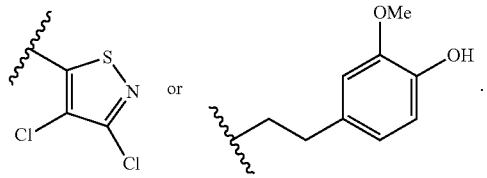 [SMILES: *c1snc(Cl)c1Cl ; "or" ; *CCc1ccc(O)c(OC)c1 ; "."]

2. A compound of the following formula IV:

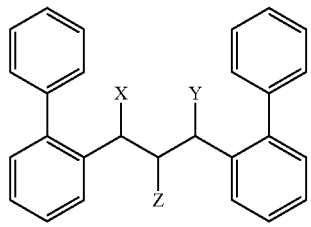

IV wherein X is chosen from O, S, or N;

Y is chosen from O, S, or N;

Z is a substituted or unsubstituted alkyl group;

wherein none of the groups X, Y, or Z is connected to Z by a covalent bond;

each position on the biphenyl rings depicted in formula IV is chosen from H or a biphenyl substituent; and and wherein "biphenyl substituent" is chosen from a substituted or unsubstituted C1-C24 alkyl, a substituted or unsubstituted aryl group, or $OSiQ_3$.

3. The compound of claim 1, having each of the groups X and Y bonded to a single metal atom;

wherein said single metal atom is chosen from Li, Na, K, Rb, Cs, Be, Mg, Ca, Sr, Ba, Sc, Y, La, Ti, V, Cr, Mn, Fe, Co, Ni, Cu, Zn, Zr, Nb, Mo, Ru, Rh, Pd, Ag, Cd, Hf, Ta, W, Re, Os, Ir, Pt, Au, Al, Ga, In, Tl, Ge, Sn, Pb, P, As, Sb, and Bi.

4. The compound of claim 2, having each of the groups X and Y bonded to a single metal atom;

wherein said single metal atom is chosen from Li, Na, K, Rb, Cs, Be, Mg, Ca, Sr, Ba, Sc, Y, La, Ti, V, Cr, Mn, Fe, Co, Ni, Cu, Zn, Zr, Nb, Mo, Ru, Rh, Pd, Ag, Cd, Hf, Ta, W, Re, Os, Ir, Pt, Au, Al, Ga, In, Tl, Ge, Sn, Pb, P, As, Sb, and Bi.

* * * * *